(12) United States Patent
Egnelöv

(10) Patent No.: US 11,304,791 B2
(45) Date of Patent: Apr. 19, 2022

(54) MEDICAL IMPLANT FOR REGENERATION OF TISSUE

(71) Applicant: NOVUS SCIENTIFIC AB, Uppsala (SE)

(72) Inventor: Per Egnelöv, Uppsala (SE)

(73) Assignee: NOVUS SCIENTIFIC AB, Uppsala (SE)

(*) Notice: Subject to any disclaimer, the term of this patent is extended or adjusted under 35 U.S.C. 154(b) by 100 days.

(21) Appl. No.: 16/496,529

(22) PCT Filed: Mar. 22, 2018

(86) PCT No.: PCT/EP2018/057240
§ 371 (c)(1),
(2) Date: Sep. 23, 2019

(87) PCT Pub. No.: WO2018/177858
PCT Pub. Date: Oct. 4, 2018

(65) Prior Publication Data
US 2020/0375715 A1 Dec. 3, 2020

(30) Foreign Application Priority Data
Mar. 29, 2017 (SE) .................... 1750370-7

(51) Int. Cl.
*A61F 2/00* (2006.01)
(52) U.S. Cl.
CPC .... *A61F 2/0063* (2013.01); *A61F 2210/0004* (2013.01); *A61F 2230/0093* (2013.01); *A61F 2250/0067* (2013.01)

(58) Field of Classification Search
CPC ............ A61F 2/0063; A61F 2230/0091; A61F 2002/3093; A61L 27/14
See application file for complete search history.

(56) References Cited

U.S. PATENT DOCUMENTS

| 5,397,331 A | 3/1995 | Himpens et al. |
| 8,083,755 B2 | 12/2011 | Mathisen et al. |
| 9,566,370 B2 | 2/2017 | Mathisen et al. |

(Continued)

FOREIGN PATENT DOCUMENTS

| EP | 2 626 454 A1 | 8/2013 |
| FR | 3 006 580 A1 | 12/2014 |

(Continued)

*Primary Examiner* — Brian A Dukert
*Assistant Examiner* — Rebecca Lynee Zimmerman
(74) *Attorney, Agent, or Firm* — Foley & Lardner LLP

(57) ABSTRACT

The present disclosure is directed to a medical implant (20) comprising: —a coil-shaped component (21) and —a first mesh component (22) and a second mesh component (23); wherein each mesh component has a largest surface extending in two directions in the x-y plane of the mesh component, and wherein each mesh component has a projected area, which is said largest surface as projected in the x-y plane of the medical implant; wherein the coil-shaped component is arranged between the two mesh components; wherein the coil-shaped component has a center core which is hollow; and wherein the coil-shaped component has a helix rotation axis, which extends in parallel with said projected area of the first mesh component and said projected area of the second mesh component.

16 Claims, 10 Drawing Sheets

(56) References Cited

U.S. PATENT DOCUMENTS

| | | | |
|---|---|---|---|
| 2003/0036797 A1* | 2/2003 | Malaviya | A61F 2/30756 623/14.12 |
| 2004/0171321 A1* | 9/2004 | Plant | A41D 31/285 442/64 |
| 2014/0081296 A1* | 3/2014 | Palmer | A61F 2/0063 606/151 |
| 2014/0222161 A1 | 8/2014 | Mathisen | |
| 2015/0238301 A1 | 8/2015 | Hingston et al. | |

FOREIGN PATENT DOCUMENTS

| WO | WO 2015/104014 A1 | 7/2015 |
|---|---|---|
| WO | WO 2016/037065 A1 | 3/2016 |
| WO | WO 2017/050837 A1 | 3/2017 |

\* cited by examiner a b c a b c a b c a b a b a b c

MEDICAL IMPLANT FOR REGENERATION OF TISSUE

FIELD OF THE INVENTION

The present disclosure relates to the field of medical technology, in particular to a medical implant, the main object of which is to facilitate regeneration of tissue, in particular soft tissue, in three dimensions in the body of an individual. The medical implant comprises a coil-shaped component arranged between two mesh components.

BACKGROUND OF THE INVENTION

Within the area of medical surgery, there is a large number of medical operations and treatments that require support during wound healing and subsequently tissue regeneration. A porous three-dimensional (3D) support is sometimes beneficial in order to efficiently accomplish tissue regeneration in three dimensions. It is also in some applications beneficial to have a temporary support, a support that degrades while the tissue regenerates. Degradable polymers, such as polyesters and polycarbonates have been used for decades in medical devices. The advantage with the degradable polymers is that the body can take care of and excrete the degradation products.

Examples of techniques that have been used to fabricate three-dimensional scaffolds are solvent-casting particulate-leaching, gas foaming, electro-spinning, phase separation, melt molding, emulsion freeze drying, solution casting, as well as freeze drying. However, these conventional methods have many limitations; limitations related to reproducibility, difficulties to achieve and design exact pore size, interconnectivity and mechanical properties. The methods have been improved during the last decade and new techniques include for example 3D-printing, 3D-knitting and bio-printing. In comparison to the older methods, 3D printing enables the possibility to produce scaffolds with complex designs which in turn allows homogenous cell distribution. One of the current disadvantages is the production time, which may increase further as the scaffold design becomes more precise and complex.

In addition to the design, which includes pore size, porosity, and interconnectivity, also the mechanical properties of the 3D scaffold are of highest importance. Upon implantation, the scaffold will interact immediately with proteins in the body and will subsequently interact with the cells surrounding the scaffold. Dependent on the mechanical properties of the scaffold at the time of implantation and during degradation, the cell proliferation and differentiation will be influenced to a great extent. The mechanical properties are also important from a usability perspective; it should for example be possible to place the scaffold at the defect area without any problem and the patient should have a pleasant feeling after the surgery.

There is a need for new adaptable, preferably degradable, 3D scaffolds, the mechanical properties of which are easy to design and to vary, depending on the intended clinical application. More particularly, there is a need for a scaffold, which is easy to bend and which during bending maintains its 3D volume (i.e. maintains its height in the z-direction), while being pliable and soft in the x-direction and in the y-direction of the scaffold.

SUMMARY OF THE INVENTION

Consequently, there is still a need for further three-dimensional medical implants having a structure which allows rapid tissue ingrowth in combination with possessing adequate pliability and mechanical rigidity for different implant applications within the human or animal body.

The above objectives are achieved by the present disclosure, which is directed to a medical implant, the main object of which is to facilitate regeneration of tissue, in particular soft tissue, in three dimensions (in an x-y-z plane) in the body of an individual.

The medical implant comprises a coil-shaped component, a first mesh component and a second mesh component, wherein each mesh component has a largest surface extending in two directions in the longitudinal plane (i.e. the x-y plane) of the mesh component, and wherein each mesh component has a projected area, which is said largest surface as projected in the x-y plane of the medical implant, where the x-y plane of the medical implant coincides with the x-y plane of the mesh components; and further wherein the coil-shaped component is arranged between the two mesh components, the coil-shaped component has a center core which is hollow, and the coil-shaped component has a helix rotation axis, which extends in parallel with said projected area of the first mesh component and said projected area of the second mesh component.

Preferred embodiments of the present disclosure are described in the dependent claims.

DETAILED DESCRIPTION OF THE INVENTION

Figure 1:
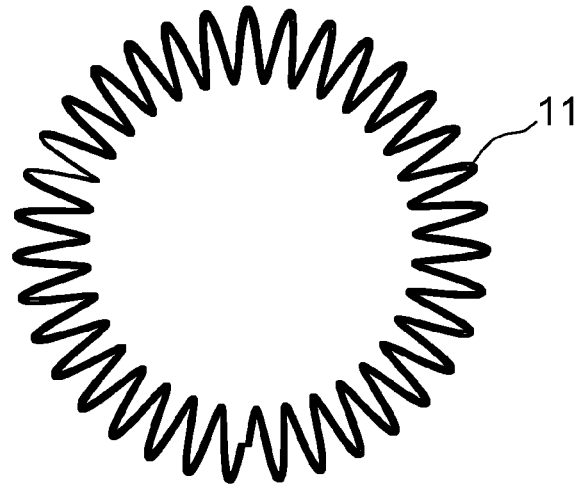
FIG. 1 illustrates an arrangement of a coil-shaped component, and a medical implant consisting of one coil-shaped component and two mesh components.
Figure 1:
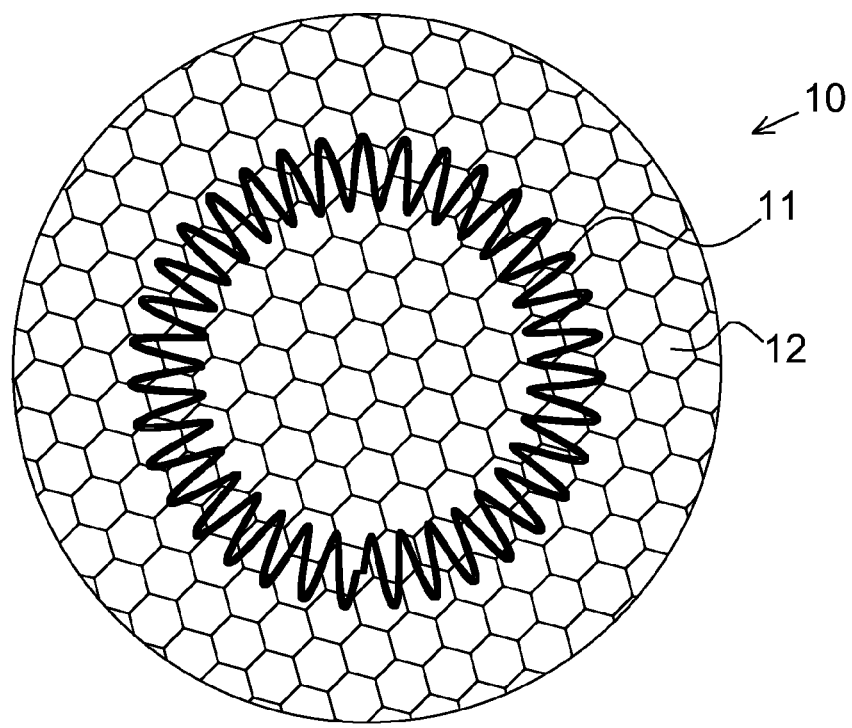
Figure 1:
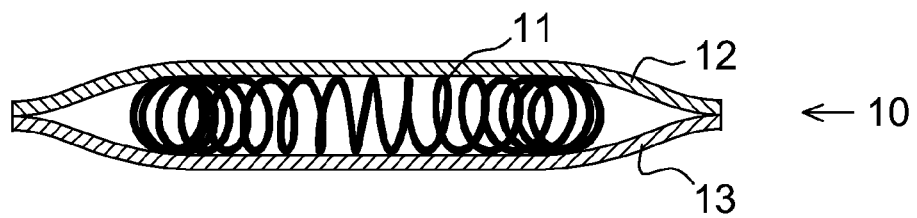

The present disclosure is directed to a medical implant which comprises a coil-shaped component and two mesh components. Each coil-shaped component is arranged between two mesh components, such that each coil-shaped component is enclosed by or at least contained between two mesh components.

For the purpose of the present disclosure, the following definitions, designs and properties of the medical implant and its components, shall apply generally.

Coil-Shaped Component

The coil-shaped component comprises a fiber component, which has been helically wound into a coil (or spiral) which has a certain length in the axial direction and which has a certain diameter, a certain coil segment profile, and a certain cross-sectional profile in the radial direction. The diameter of the coil-shaped component may be constant or may vary in size along the axial direction of the coil-shaped component. The coil segment profile and/or the cross-sectional profile of the coil-shaped component may be constant or may vary in size and/or in form or shape along the axial direction of the coil-shaped component. The coil-shaped component comprises a hollow center core, i.e. an empty space in its center. The diameter or width of the center core may be constant or may vary in the axial direction of the coil-shaped component. The cross-sectional profile of the coil-shaped component has a hollow center core area, which is larger than the cross-sectional area of the fiber component which forms the coil-shaped component. The coil-shaped component is open at its two ends in the axial direction. The coil-shaped component has a helix rotation axis which can have any one of the following forms: straight, curved, spiral, S-shape or any other suitable form or combinations thereof. The helix rotation axis may extend in the x-direction, the y-direction and/or the z-direction. The form of the helix rotation axis corresponds to the overall form of the coil-shaped component.

A coil-shaped component according to the present disclosure builds distance between two mesh components. If exposed to external forces from the surrounding tissue, it shall, to a large extent, be able to keep its originally created coiled profile and projected area. In its radial direction, the coil-shaped component shall preferably be compressed less than 50% under normal conditions in the body. When the exposure to an external, compressional force ends, the coil-shaped component shall return to its original form. However, it shall not be completely stiff but shall have certain flexibility, elasticity, and pliability in the z direction. This means that it can adapt its form in the z direction when exposed to external forces from surrounding tissue. Further, a coil-shaped component shall be able to elongate in its axial direction at least as much as, or more than, the mesh components in the x-y plane, such that the coil-shaped component does not limit the elongation of the mesh components.

Helical Pitch

The helical pitch of a coil-shaped component is defined as the distance (or space) between each helical turn of the coil. The coil-shaped component preferably has a helical pitch which is larger than the diameter or width of the fiber, wherein said diameter or width is measured in the direction of the helix rotation axis.

Envelope Surface

The envelope surface of a coil-shaped component is defined as the outer surface in the axial direction of the coil-shaped component. The envelope surface consists of the outward (or external) parts of the surface of the fiber component.

Coil Segment

A coil segment is the coil of one helical turn (360 degrees) in the axial direction of the coil-shaped component.

Mesh Component

A mesh component is a mesh knitted from one or more different fiber components.

The mesh structure comprises a mesh material having a largest surface extending in two directions and a thickness extending in a third direction that is different from the two directions. In other words, the mesh component has a largest surface extending in two directions in the longitudinal plane (i.e. the x-y plane), and a thickness extending in a third direction in a transversal plane (i.e. in the z-direction) of the mesh component. The outer boundary of the largest surface can have any suitable contour shape. The mesh component is soft and has a high pliability and flexibility, such that its largest surface can be folded, and the mesh component is easily adapted to the underlying structure. The mesh component has certain elasticity in the x-y plane.

Fiber Component

A fiber component is the component, from which a coil-shaped component is produced, built or formed. A fiber is also the component which is knitted into a mesh component.

Distance-Building Component

A distance-building component is a coil-shaped component located between two mesh components. The coil-shaped component creates a distance between the two mesh components.

Medical Implant

A medical implant according to the present disclosure comprises a coil-shaped component and two mesh components. Each coil-shaped component is located between two mesh components, such that each coil-shaped component is enclosed by or contained between or fixed between or attached between two mesh components. The coil-shaped component creates a distance between two mesh components in a medical implant according to the present disclosure. Thus, the coil-shaped component is a distance-building component, which will help create or build new volume in the body of an individual in which the medical implant is implanted.

The coil-shaped component has a helix rotation axis which extends in parallel with the projected area in the longitudinal plane (i.e. the x-y plane) of the two mesh components which enclose the coil-shaped component.

The medical implant according to the present disclosure is flexible and/or pliable in the z-direction. Thereby it will adapt its overall form in the z direction according to the surrounding tissues in the body when implanted. This property of the medical implant is dependent on the pliability and/or flexibility of the coil-shaped component and the mesh components, which are described in more detail elsewhere herein.

Projected Area

If a light were projected on a component, the shadow of the component (cast on an imaginary flat surface at the end of the component, said flat surface extending in a direction perpendicular to the direction of the light beam) corresponds to the projected area of said component. In other words, the projected area refers to the two-dimensional area of the projected image of a component onto the two-dimensional area of an imaginary flat surface which is perpendicular to the light beam and which is located at the opposite end of the component.

Accordingly, in the context of the present disclosure, the projected area of a mesh component refers to the two-dimensional area of the projected image of the mesh component onto the two-dimensional area of an imaginary flat surface which extends in the longitudinal plane, i.e. in the x-y plane of the mesh component. In other words, if a light is projected perpendicularly to the longitudinal (x-y) direction of the mesh component, the shadow of the mesh component (cast on an imaginary flat surface at the end of the component, said flat surface extending in the longitudinal (i.e. x-y) direction of the mesh component) corresponds to the projected area of said mesh component.

The term projected area of a mesh component is relevant in relation to the porosity of the mesh component. Porosity of a mesh component is measured by taking high contrast black and white photography of the mesh component and to define the area of the open pores, white pixels, relative the total area of the mesh component, where the non-porous surface of the mesh component is seen as black pixels. The total area corresponds to the projected area of the mesh component. It is thereby possible to obtain a measure of the porosity of the projected area of a mesh component.

Further, the projected area of a coil-shaped component herein refers to the two-dimensional area of the projected image of a coil-shaped component onto the two-dimensional area of an imaginary flat surface extending in the radial direction of the coil-shaped component, wherein said flat surface is located at the end of the coil-shaped component. That is, if a light is projected in the axial direction of the coil-shaped component, the shadow of the component (cast on an imaginary flat surface at the end of the coil-shaped component, said flat surface extending in the radial direction of the coil-shaped component) corresponds to the projected area of said component.

The above general definition of a projected area also applies to the projected area of a segment of a component, except that in this case the imaginary flat surface is located at the end of said segment of a component.

Accordingly, the projected area of a coil segment refers to the two-dimensional area of the projected image of a coil segment onto the two-dimensional area of an imaginary flat surface extending in the radial direction of the coil segment, wherein said flat surface is located at the end of the coil segment.

The projected area of a coil segment may have a profile (e.g. size, form) that is identical to or different from the projected area of other coil segments of the coil-shaped component. In other words, the projected area of the coil segments may vary or may be constant along the helix rotation axis of the coil-shaped component.

The projected area of a coil segment of the coil-shaped component may have a profile that is circular, semicircular, or any other shape, such as any irregular shape.

It is to be understood that, according to the present disclosure, one or more coil-shaped components may be arranged between a first mesh component and a second mesh component, wherein the number of coil-shaped components between two mesh components is in a range including from 1 to 100 coil-shaped components, such as but not limited to 1, 2, 3, 4, 5, 6, 7, 8, 9, 10, 15, 20, 30, 40, 50, 60, 70, 80, 90 or 100 coil-shaped components. Said coil-shaped components may be formed and arranged in various ways, as described in more detail elsewhere herein. One or more coil-shaped components, which are enclosed by the same two mesh components, may be said to constitute an arrangement of coil-shaped components.

The figures illustrate various arrangements of coil-shaped components and medical implants comprising coil-shaped components arranged between mesh components. Since the mesh components are porous, a coil-shaped component which is located between two mesh components can be partly seen through the mesh components. However, to keep all top view figures clear and reproducible, all coil-shaped components have been drawn with solid lines instead of dashed lines, although the coil-shaped components are located behind a mesh component in the top view figures. Since the mesh components are porous, also a second mesh component, which is located behind both a coil-shaped component and a first mesh component, can be partly glimpsed through the first mesh component (i.e. those parts which are not hidden behind the coil-shaped component). However, again, to keep all top view figures clear and reproducible, any mesh component which is located behind a coil-shaped component and another mesh component is not shown in the top view figures but only in the corresponding side view figures.

FIG. 1 illustrates an arrangement of a coil-shaped component, and a medical implant consisting of one coil-shaped component and two mesh components. FIG. 1a is a top view of a coil-shaped component 11, which is formed as a circle. FIG. 1b is a top view of a medical implant 10 and shows a coil-shaped component 11 and a first mesh component 12. The first mesh component 12 is located in front of the coil-shaped component 11. The medical implant 10 further comprises a second mesh component 13, which in the top view according to FIG. 1b is located behind the coil-shaped component 11 and the first mesh component 12. As explained above in relation to all top view figures, the second mesh component 13 is not shown in FIG. 1b for reasons of clarity and reproducibility of the figure. FIG. 1c is a side view of the medical implant 10 consisting of the coil-shaped component 11, which is located between and enclosed by the first mesh component 12 and the second mesh component 13. In this embodiment, as well as in all other embodiments where a coil-shaped component is formed as a circle, the two ends of the coil-shaped component may be arranged to meet, with or without attachment to each other. The two ends may be attached to each other by any suitable attachment technique. Alternatively, the two ends may be arranged such that they do not completely meet but are separated by a distance, such as, but not limited to, in a range of including from 0.1 to 1 helical pitch of said coil-shaped component.

Figure 2:
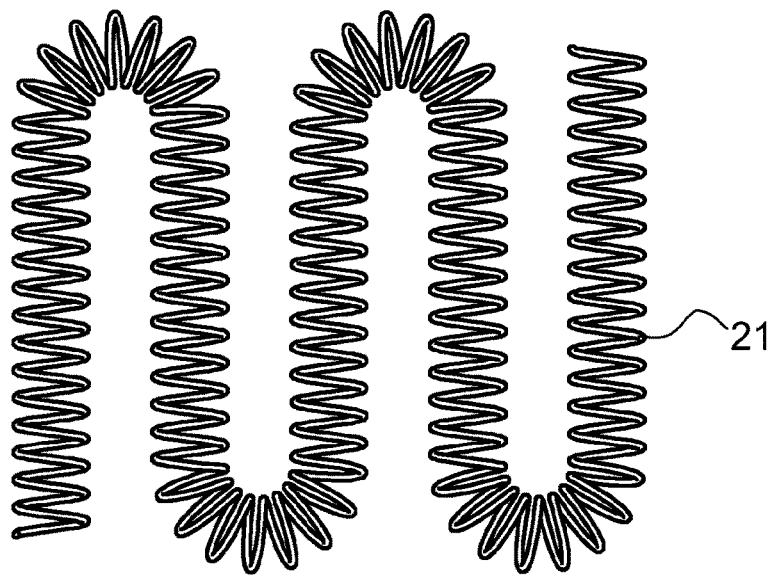
FIG. 2 depicts an arrangement of a coil-shaped component, and a medical implant consisting one coil-shaped component and two mesh components.
Figure 2:
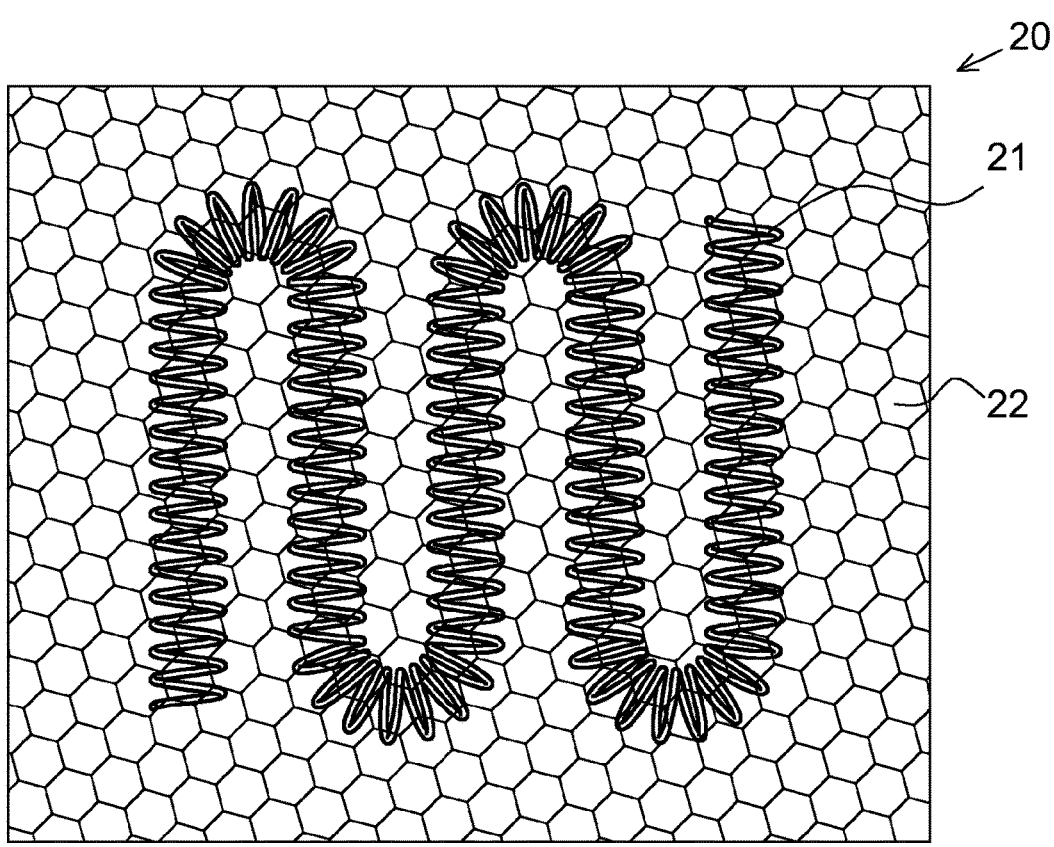
Figure 2:
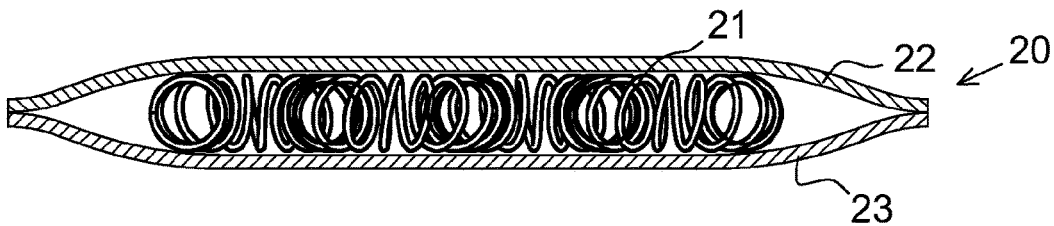

FIG. 2 depicts another arrangement of a coil-shaped component, and a medical implant consisting one coil-shaped component and two mesh components. FIG. 2a is a top view of a coil-shaped component 21 having an S-form. FIG. 2b is a top view of a medical implant 20 and shows said coil-shaped component 21 and a first mesh component 22. The first mesh component 22 is located in front of the coil-shaped component 21. The medical implant 20 further comprises a second mesh component 23, which in the top view according to FIG. 2b is located behind the coil-shaped component 21 and the first mesh component 22. As explained above in relation to all top view figures, the second mesh component 23 is not shown in FIG. 2b for reasons of clarity and reproducibility of the figure. FIG. 2c is a side view of the medical implant 20 consisting of the coil-shaped component 21 arranged between and enclosed by the first mesh component 22 and the second mesh component 23.

It is to be understood that, according to the present disclosure, a coil-shaped component can be formed into any suitable form or shape, in a plane parallel to the projected areas of the mesh components. Said form or shape fills out space and creates distance between two mesh components. Examples of such forms or shapes include, but are not limited to, a circle, an oval, a rectangle, an S-form, a straight line, a U-turn, and any type of formable form or shape. The coil-shaped component can be formed in different ways, and can be arranged to cover more or less of the projected area of the mesh components, depending on which function the medical implant shall have, or which application the medical implant is intended for, in the body.

In FIG. 1, the contour shape of the mesh components is circular, which is matched by the circular form of the coil-shaped component. In FIG. 2, the contour shape of the mesh components is rectangular, and the coil-shaped component is formed into an S-form to match the contour shape of the mesh components. It is to be understood that a mesh component according to the present disclosure can have any suitable contour shape, such as but not limited to a circle, an oval, a rectangle, a square, or a semicircle. The two or more mesh components included in a medical implant may have an identical contour shape or different contour shapes; however it is presently preferred that all mesh components of a medical implant have an identical contour shape. Further, it is presently preferred that the outer boundary of an arrangement of one or more coil-shaped components matches the contour shape and the size of the two surrounding mesh components. Thereby, the arrangement of coil-shaped components creates the desired distance between most of the two mesh components.

Figure 3:
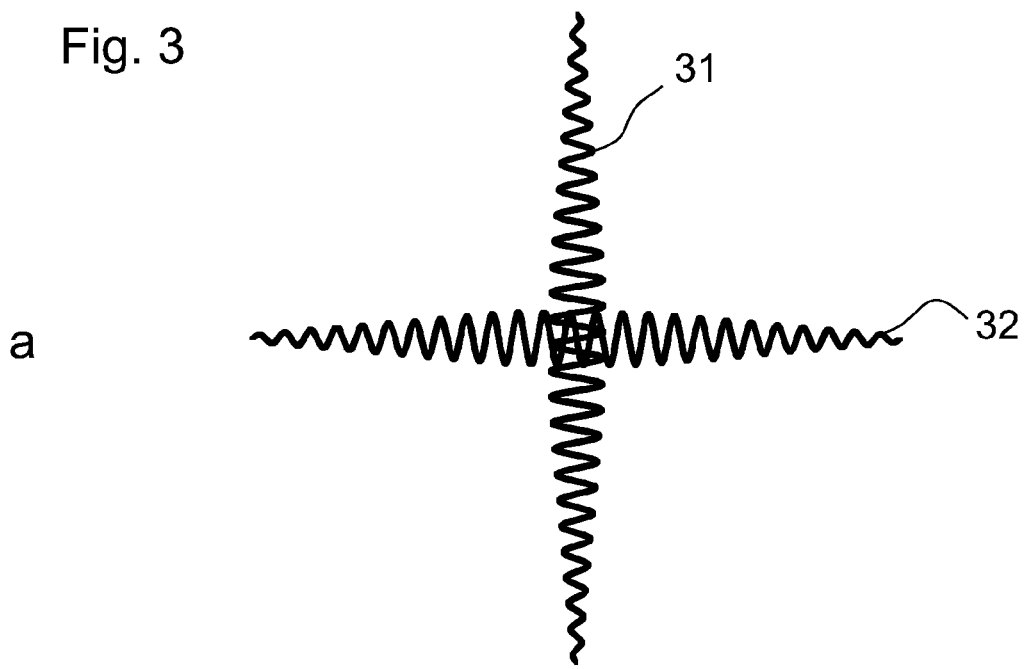
FIG. 3 shows an arrangement of two coil-shaped components, and a medical implant comprising two coil-shaped components and two mesh components.
Figure 3:
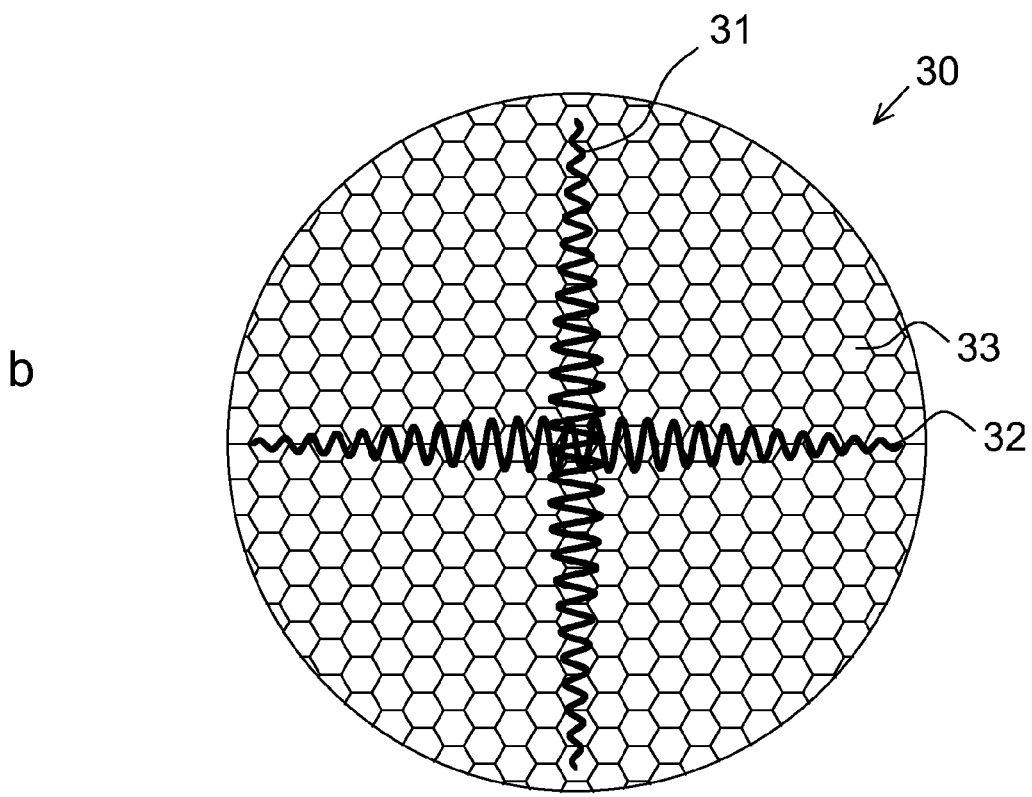
Figure 3:
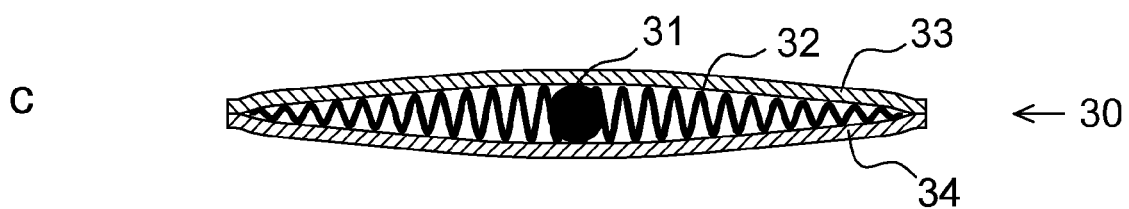

FIG. 3 shows an arrangement of two coil-shaped components, and a medical implant comprising two coil-shaped components and two mesh components. FIG. 2a is a top view of a first coil-shaped component 31 and a second coil-shaped component 32, which are arranged axially perpendicular and which intersect each other at the center. FIG. 3b is a top view of a medical implant 30 and shows the first coil-shaped component 31 and the second coil-shaped component 32 intersecting each other, and further shows a first mesh component 33. The first mesh component 33 is located in front of the coil-shaped components 31 and 32. The medical implant 30 further comprises a second mesh component 34, which in the top view according to FIG. 3b is located behind the coil-shaped components 31 and 32 and the first mesh component 33. The second mesh component 34 is not shown in FIG. 3b for reasons of clarity and reproducibility of the figure. FIG. 3c is a side view of the medical implant 30 consisting of the two coil-shaped components 31 and 32, enclosed by the two mesh components 33 and 34.

Figure 4:
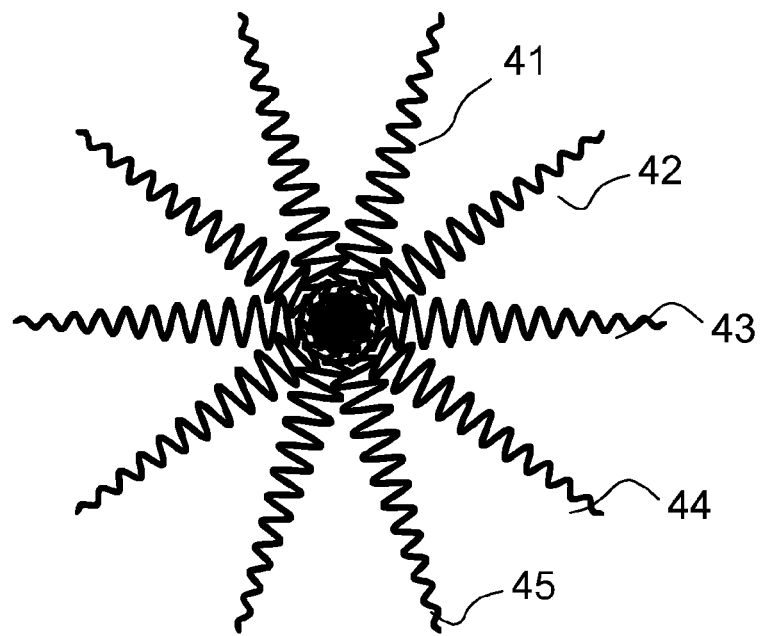
FIG. 4 illustrates alternative arrangements of coil-shaped components.
Figure 4:
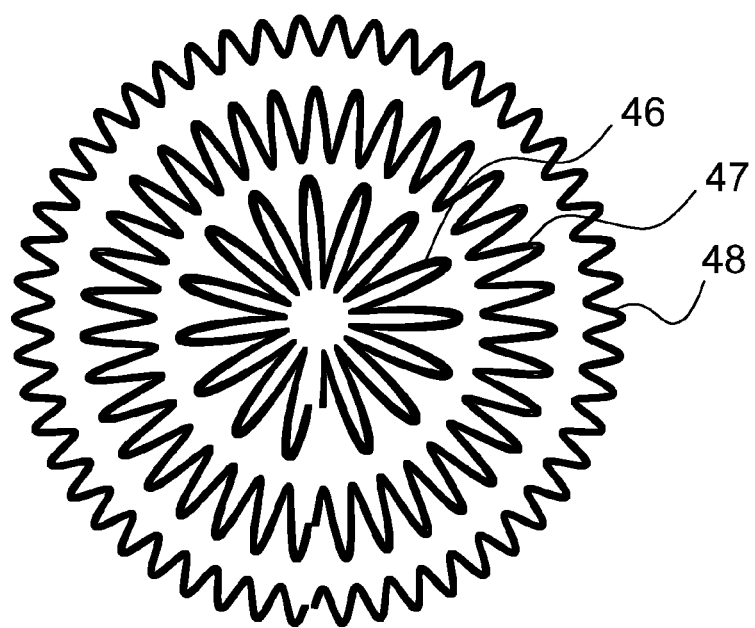

FIG. 4 illustrates further arrangements of coil-shaped components, each of which may be included in a medical implant according to the present disclosure. FIG. 4a is a top view of an arrangement of a first coil-shaped component 41, a second coil-shaped component 42, a third coil-shaped component 43, a fourth coil-shaped component 44, and a fifth coil-shaped component 45, which intersect each other at the center and are arranged axially at an angle between 0° and 90° in relation to each other. Said arrangement of coil-shaped components can be enclosed between two mesh components, thereby forming a medical implant according to the present disclosure. FIG. 4b is a top view of an arrangement of a first coil-shaped component 46, a second coil-shaped component 47, and a third coil-shaped component 48. Each coil-shaped component is formed as a circle. The coil-shaped components are arranged separately from each other, locating the smallest circle 46 innermost and the largest circle 48 outermost, with circle 47 between the smaller circle and the larger circle. Such an arrangement of coil-shaped components can be arranged between two mesh components, thereby forming a medical implant according to the present disclosure. FIG. 4b shows an embodiment where there is a distance between each of the coil-shaped components 46, 47 and 48. Alternatively, the coil-shaped components may be arranged such that the envelope surfaces of each two coil-shaped components meet. The coil-shaped components may be arranged next to each other without any distance in-between or they may overlap in one plane parallel to the projected areas of the mesh components, e.g. by being partially intertwined. In this type of arrangement, partially intertwined shall be taken to mean that a part or all of a helical turn of an inner coil-shaped component is arranged inside a helical turn of an outer coil-shaped component. Two coil-shaped components which are partially intertwined may overlap in one or more helical turns.

Figure 5:
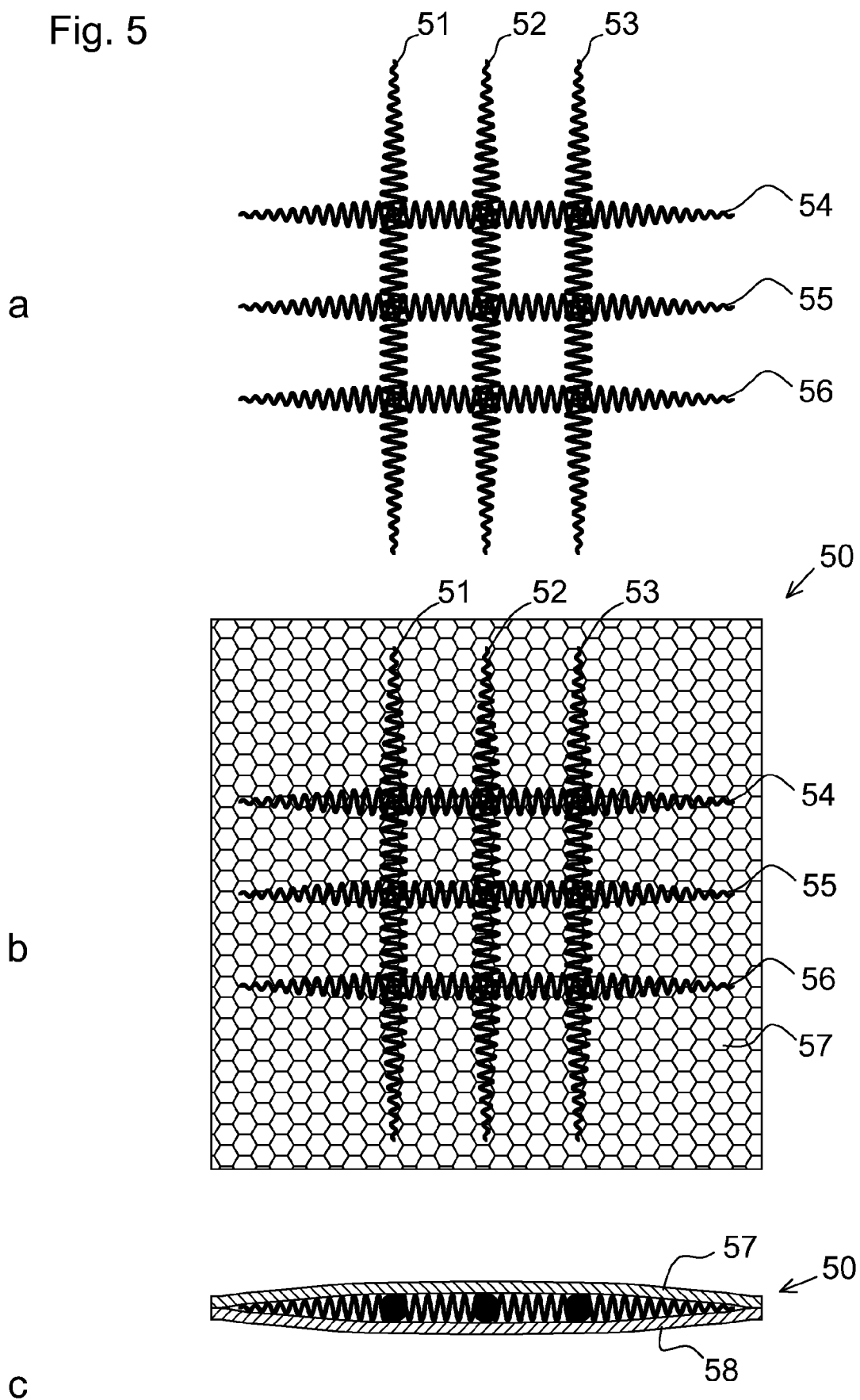
FIG. 5 depicts an arrangement of six coil-shaped components, and a medical implant comprising six coil-shaped components and two mesh components.

FIG. 5 depicts an arrangement of six coil-shaped components, and a medical implant comprising six coil-shaped components and two mesh components. FIG. 5a is a top view of an arrangement comprising a first coil-shaped component 51, a second coil-shaped component 52, and a third coil-shaped component 53, which are arranged axially parallel. The arrangement further comprises a fourth coil-shaped component 54, a fifth coil-shaped component 55, and a sixth coil-shaped component 56, which are arranged axially parallel, and which are arranged axially perpendicular to and intersect coil-shaped components 51, 52, and 53. FIG. 5b is a top view of a medical implant 50 and shows the coil-shaped components 51-56 intersecting each other, and further shows a first mesh component 57. The first mesh component 57 is located in front of the coil-shaped components 51-56. The medical implant 50 further comprises a second mesh component 58, which is not shown in FIG. 5b for reasons as explained above. FIG. 5c is a side view of the medical implant 50 consisting of the six coil-shaped components 51-56, arranged between and enclosed by the two mesh components 57 and 58.

Figure 6:
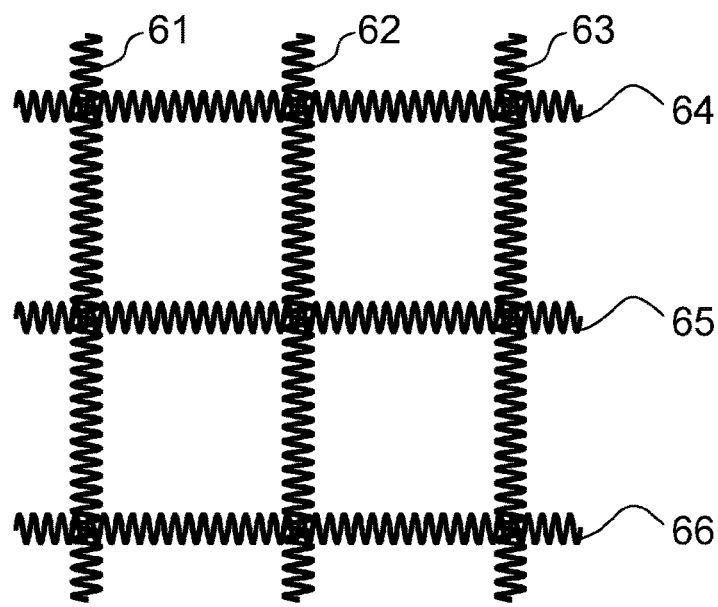
FIG. 6 illustrates an arrangement of six coil-shaped components and a medical implant comprising several layers of coil-shaped components and mesh components.
Figure 6:
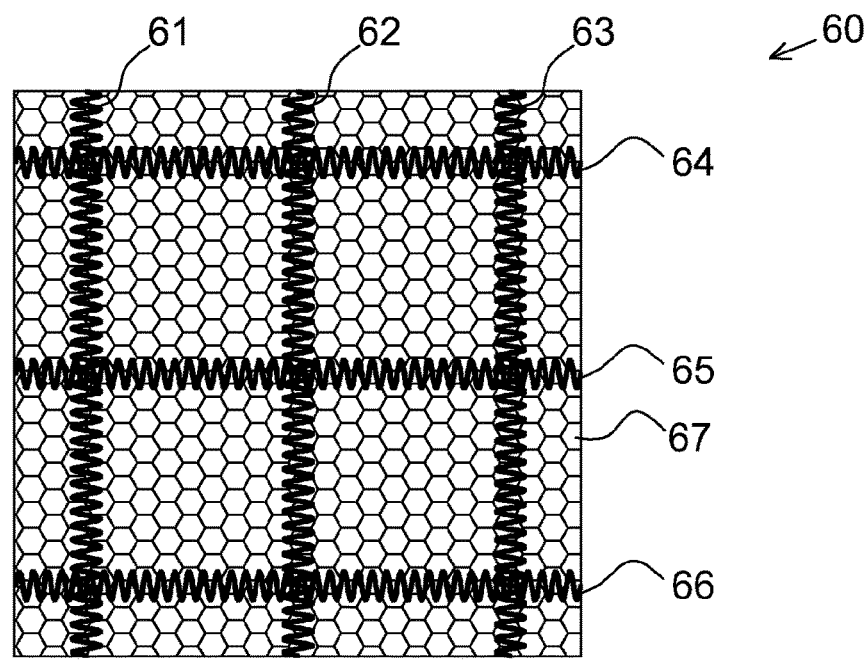
Figure 6:
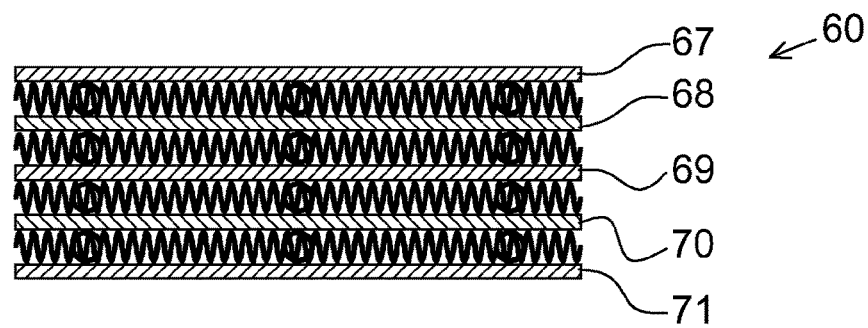

FIG. 6 illustrates another arrangement of six coil-shaped components, and further illustrates a medical implant comprising several layers of coil-shaped components and mesh components. In total, the medical implant shown in FIG. 6 includes four identical arrangements of six coil-shaped components each and five mesh components. FIG. 6a is a top view of a first arrangement comprising a first coil-shaped component 61, a second coil-shaped component 62, and a third coil-shaped component 63, which are arranged axially parallel. The arrangement further comprises a fourth coil-shaped component 64, a fifth coil-shaped component 65, and a sixth coil-shaped component 66, which are arranged axially parallel, and which are arranged axially perpendicular to and intersect coil-shaped components 61, 62, and 63. FIG. 6b is a top view of a medical implant 60 and shows the first arrangement of coil-shaped components 61-66 intersecting each other, and further shows a first mesh component 67. The first mesh component 67 is located in front of the coil-shaped components 61-66. The medical implant 60 further comprises a second mesh component 68, a second arrangement of six coil-shaped components 61-66, a third mesh component 69, a third arrangement of six coil-shaped components 61-66, a fourth mesh component 70, a fourth arrangement of six coil-shaped components 61-66, and a fifth mesh component 71, all of which are located behind the first mesh component 67 and the first arrangement of six coil-shaped components 61-66 and which are not shown in FIG. 6b for reasons of clarity and reproducibility of the figure. FIG. 6c is a side view of the medical implant 60 consisting of a first arrangement of six coil-shaped components 61-66 arranged between the first and second mesh components 67 and 68, a second arrangement of six coil-shaped components 61-66 arranged between the second and third mesh components 68 and 69, a third arrangement of six coil-shaped components 61-66 arranged between the third and fourth mesh components 69 and 70, and a fourth arrangement of six coil-shaped components 61-66 arranged between the fourth and fifth mesh components 70 and 71.

In the embodiment shown in FIG. 6, four identical arrangements of coil-shaped components are used, stacked as several layers between mesh components in the medical implant. A person skilled in the art readily understands that any suitable number of identical arrangements of coil-shaped components, and/or any suitable number of different arrangements of coil-shaped components, and/or any combination thereof may be included in the same medical implant. The arrangements are stacked as layers, each layer being arranged between two mesh components. Arrangements of coil-shaped components may for example differ from each other in terms of the number, size and/or forms of coil-shaped components included in each arrangement, as described in more detail elsewhere herein. The number of arrangements of coil-shaped components to be used in a medical implant depends for example on which function the medical implant shall have, and/or which application the medical implant is intended for, in the body. A suitable total number of arrangements of coil-shaped components is presently considered to be in a range including from 1 to 9, such as 1, 2, 3, 4, 5, 6, 7, 8, or 9 arrangements of coil-shaped components.

A person skilled in the art further understands that a medical implant according to the present disclosure may comprise any suitable number of mesh components, such as 2, 3, 4, 5, 6, 7, 8, 9 or 10 mesh components, stacked as layers with coil-shaped components arranged in-between each two mesh components. The number of mesh components to be used in a medical implant depends for example on which function the medical implant shall have, and/or which application the medical implant is intended for, in the body.

Figure 7:
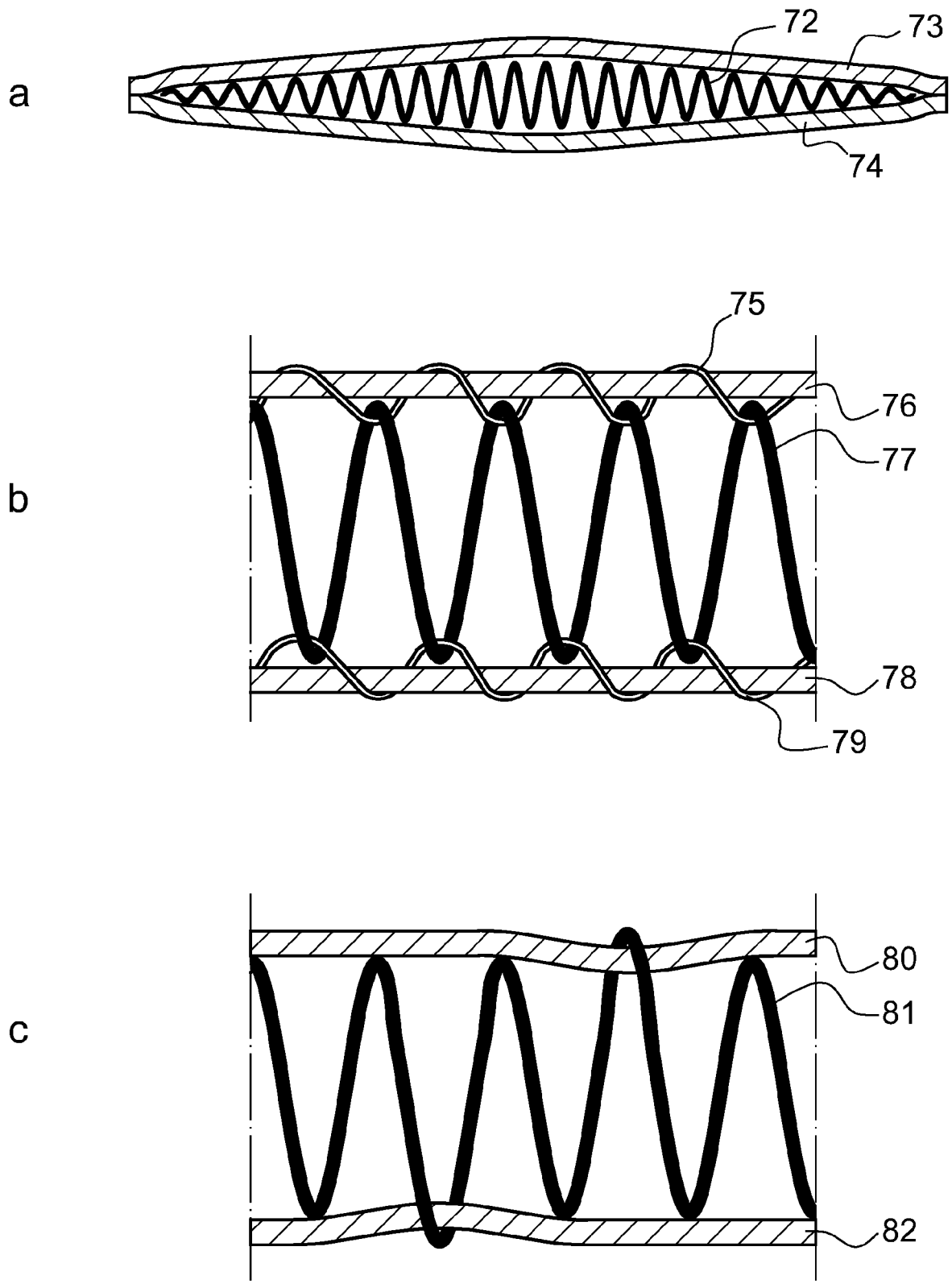
FIG. 7 depicts different ways of arranging a coil-shaped component between two mesh components.

FIG. 7 depicts different ways of arranging a coil-shaped component between two mesh components. FIG. 7a is a side view of a medical implant and shows two mesh components 73 and 74, which are attached to each other along their edges, thereby enclosing a coil-shaped component 72. For comparison, also in FIG. 1c, FIG. 2c, FIG. 3c, and FIG. 5c, the two mesh components are attached to each other along their edges with the purpose of enclosing coil-shaped components. It is to be understood that different attachment techniques or closing mechanisms can be used to attach the edges of mesh components to each other, such as but not limited to suturing, gluing, and/or stapling. Two mesh components can be directly attached to each other along some or all edges, possibly leaving suitable slots or openings, through which the medical implant can be filled with for example tissue, after which the slots or openings can be closed by suturing or other suitable closing mechanism. In contrast to FIG. 7a, FIG. 6c shows a medical implant 60 in which the ends of the mesh components are open, i.e. are not attached to each other. In such an embodiment, the coil-shaped components are kept in place between the mesh components by direct attachment of each coil-shaped component to both surrounding mesh components, e.g. by stitching. This is further illustrated by FIGS. 7b and 7c, respectively. FIG. 7b shows a part of a medical implant comprising a first mesh component 76, a second mesh component 78, and a coil-shaped component 77. The coil-shaped component 77 is attached to the first mesh component 76 by a thread 75, and is further attached to the second mesh component 78 by a thread 79. In FIG. 7b, the threads 75 and 79 attach each loop of the coil-shaped component 77 to mesh component 76 or mesh component 78, respectively. Alternatively, one or both threads may be more sparsely threaded or stitched through each mesh component, respectively, i.e. attaching less than each loop of the coil-shaped component 77 to one or both mesh components, respectively. FIG. 7c shows a part of a medical implant comprising a first mesh component 80, a second mesh component 82, and a coil-shaped component 81. The coil-shaped component 81 is attached to the first mesh component 80 and to the second mesh component 82 by threading a loop of the coil-shaped component through each mesh component, respectively. It is to be understood that attachment can be achieved by threading one or more loops of the coil-shaped component through each mesh component, respectively.

Figure 8:
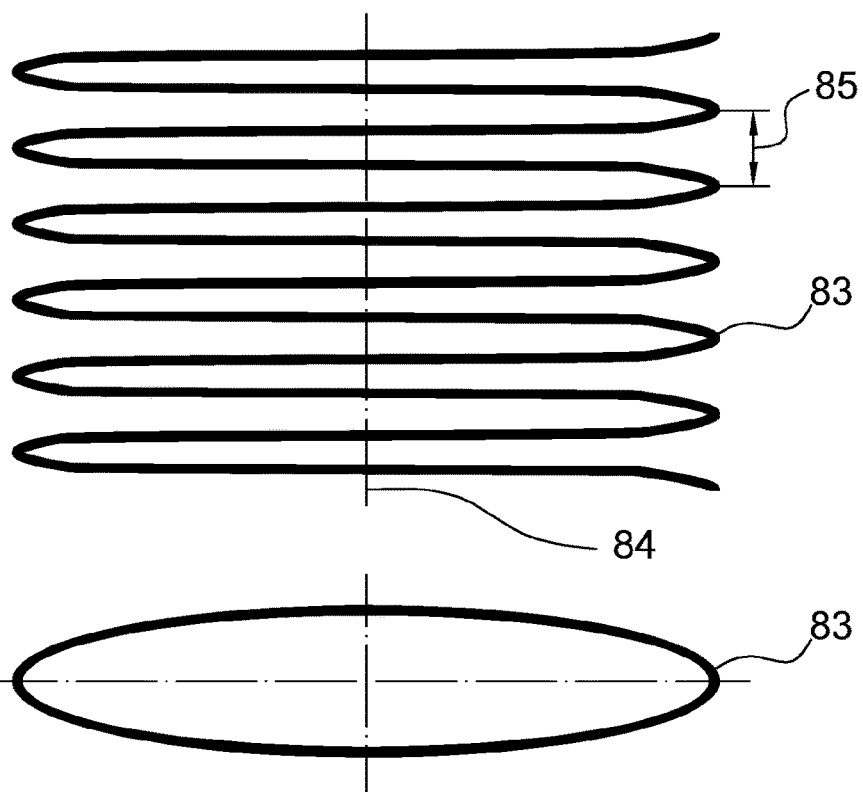
FIG. 8 shows a top view of a coil-shaped component and the projected area of a coil segment.
Figure 8:
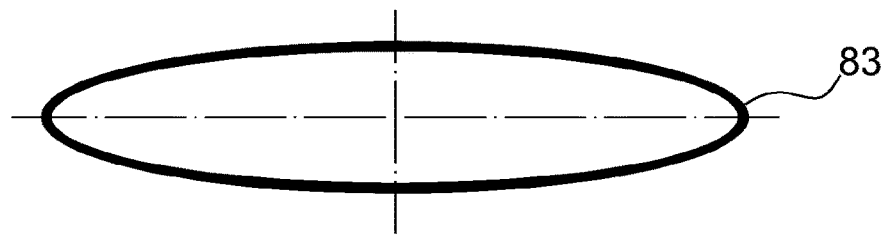
Figure 9:
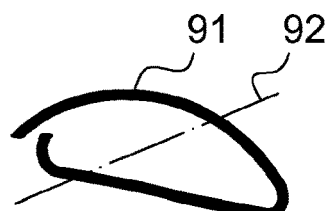
FIG. 9 illustrates alternative coil-shaped components which include coil segments having different cross-sectional profiles and/or different projected areas.
Figure 9:
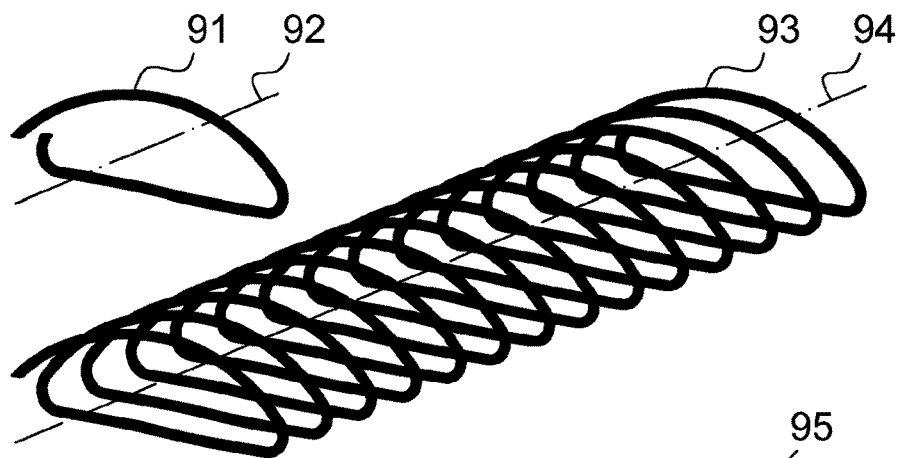
Figure 9:
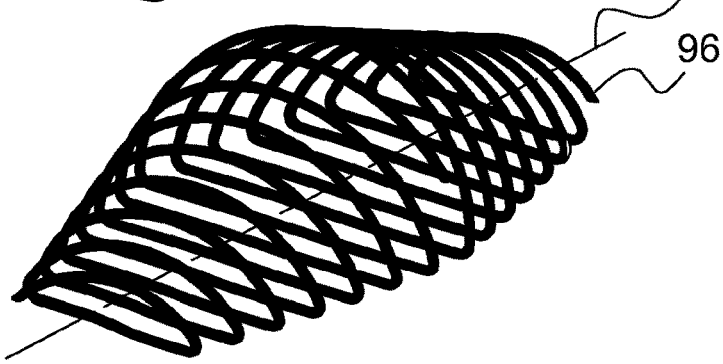

FIGS. 8 and 9 illustrate various coil-shaped components which include coil segments having different cross-sectional profiles and/or different projected areas.

FIG. 8a is a top view of a coil-shaped component 83. The helix rotation axis 84 and the helical pitch 85 (as defined elsewhere herein) of the coil-shaped component 83 are also shown. The left-hand part of FIG. 8b is a side view of the oval shape of the projected area of a coil-segment of the coil-shaped component 83.

FIG. 9a is a perspective view of a coil segment 91 and its helix rotation axis 92. The projected area of the coil segment is irregular, close to semicircular. FIG. 9a shows one coil segment 91 of a coil-shaped component 93 as depicted in FIG. 9b. The helix rotation axis 94 is also shown in FIG. 9b. The projected area is identical for each coil segment of the coil-shaped component 93. In other words, the projected area is constant along the helix rotation axis of the coil-shaped component 93. FIG. 9c is a perspective view of a coil-shaped component 96 and its helix rotation axis 95. The projected area of each coil segment has the same profile but varies in size along the helix rotation axis 95 of the coil-shaped component 96.

Figure 10:
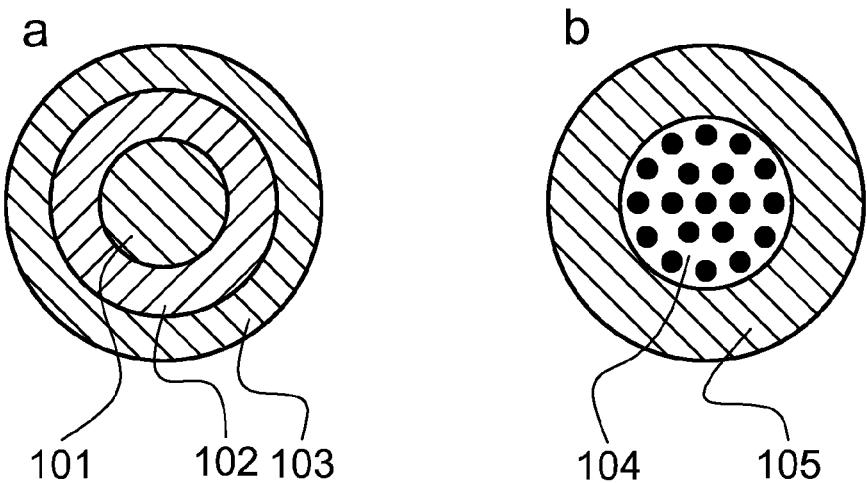
FIG. 10 illustrates various embodiments of a fiber component.

FIG. 10 illustrates various embodiments of a fiber component, which can be used both for the production of a mesh component and a coil-shaped component according to the present disclosure. FIG. 10a is a cross-sectional view showing a fiber component consisting of three layers of filaments; a mono filament 101, surrounded by a first, inner, tube filament 102 and a second, outer, tube filament 103. The tube filaments may for example be produced by extrusion, coating, shrinking or any other suitable method. Each of the filaments shown has a circular cross-sectional profile. FIG. 10b is a cross-sectional view showing a fiber component consisting of a multifilament 104 located in the center of a tube filament 105. Each of the filaments shown has a circular cross-sectional profile. FIG. 10c is a cross-sectional view showing a fiber component consisting of a tube filament 106, which has a circular cross-sectional profile. FIG. 10d is a cross-sectional view showing a fiber component consisting of a monofilament 107, which has a quadratic cross-sectional profile. Other embodiments of fiber components have been described elsewhere herein. It is to be understood that different embodiments of fiber components can be used in combination in different parts of a medical implant, such as in different parts of the same mesh component, and/or in different mesh components and/or in different coil-shaped components included in the same medical implant.

Figure 11:
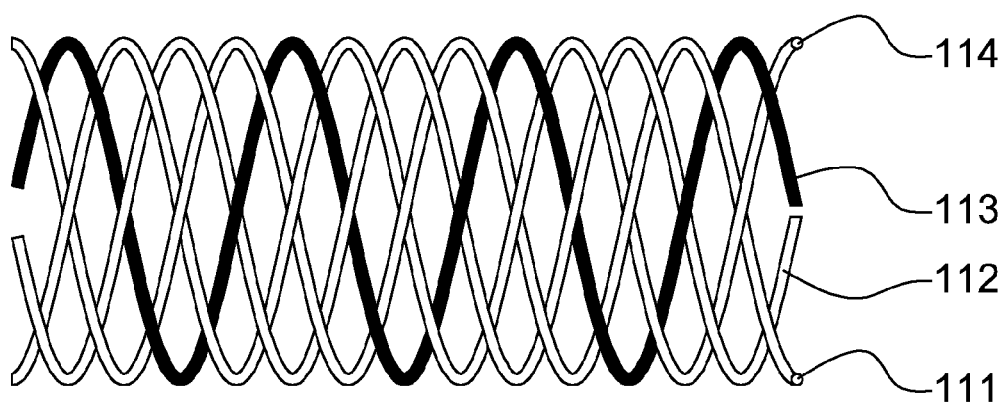
FIG. 11 shows a braided coil-shaped component.

FIG. 11 illustrates a coil-shaped component, which is formed by intertwining or braiding a first fiber 111, a second fiber 112, a third fiber 113, and a fourth fiber 114, which all have identical helical form and cross-sectional profile. Fibers 111 and 114 have the same rotational direction while fibers 112 and 113 have the opposite rotational direction.

Figure 12:
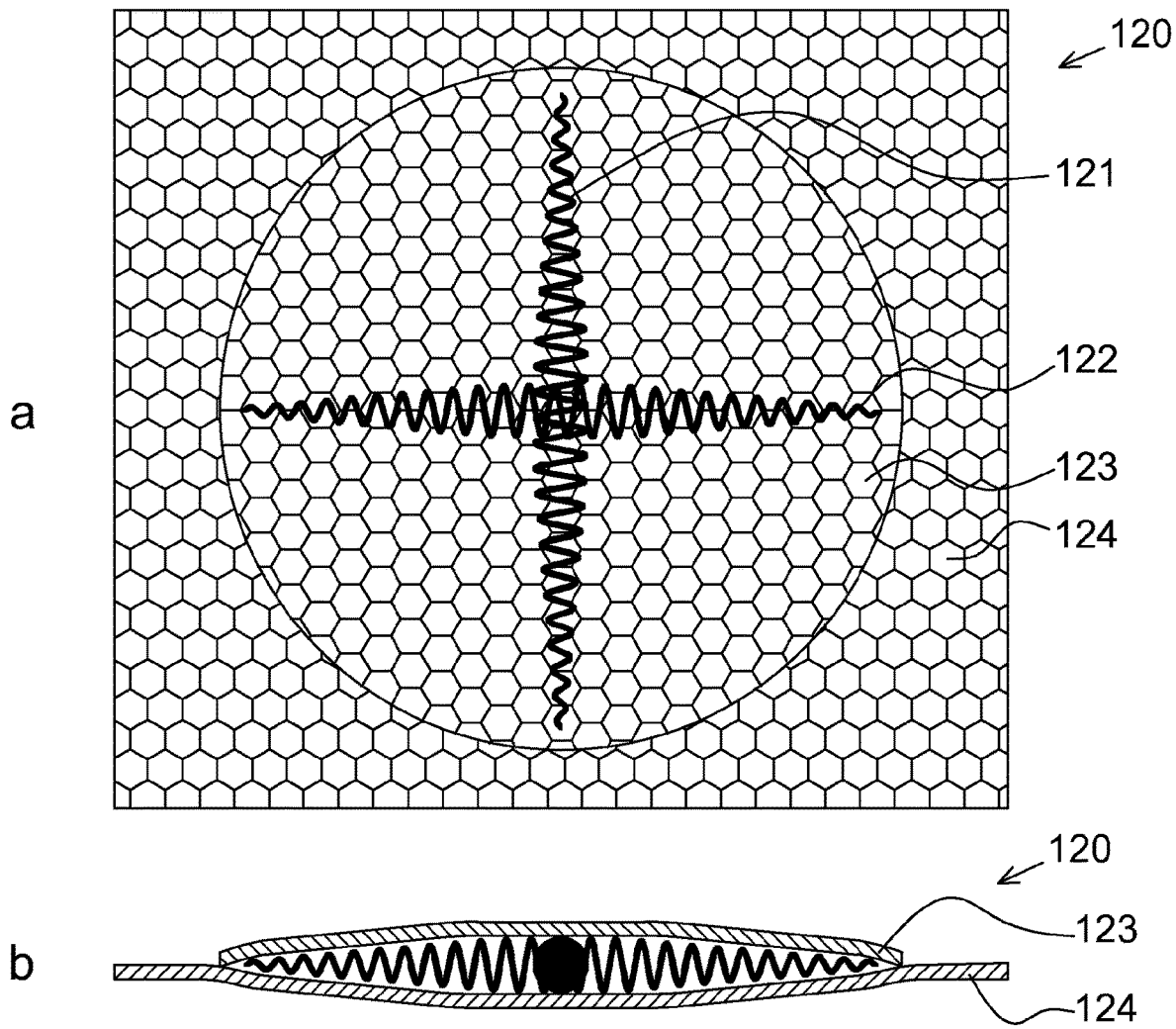
FIG. 12 depicts a medical implant wherein the mesh components have different size and contour shape.

FIG. 12 depicts a medical implant wherein the mesh components have different size and contour shape. FIG. 12a is a top view showing the medical implant 120, including two coil-shaped components 121 and 122, a first mesh component 123 and a second mesh component 124. The first mesh component 123 is circular while the second mesh component 124 is rectangular. The projected area of the first mesh component 123 is smaller than the projected area of the second mesh component 124. FIG. 12b is a side view of the medical implant 120, showing the two coil-shaped components being arranged between and being enclosed by the two mesh components, and further showing that the size of the second mesh component 124 is larger than the size of the mesh component 123.

Figure 13:
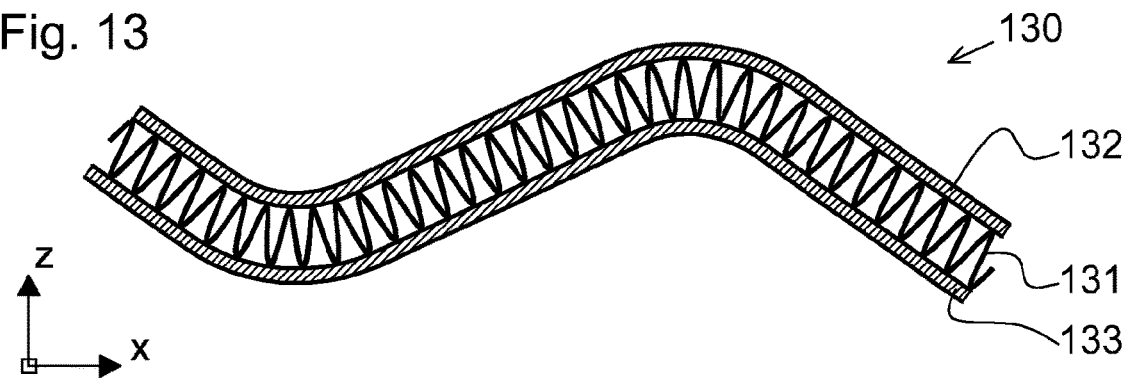
FIG. 13 illustrates the flexibility of a medical implant according to the present disclosure.

FIG. 13 illustrates that a medical implant 130, comprising a coil-shaped component 131 and two mesh components 132 and 133, is flexible and/or pliable in the z direction. Thereby it will adapt its overall form in the z direction according to the surrounding tissues in the body when implanted. This property of the medical implant is of course dependent on the pliability and/or flexibility of the coil-shaped component and the mesh components, which are described in more detail elsewhere herein.

As mentioned in relation to FIG. 7 above, between each pair of two mesh components at least one coil-shaped component is arranged or contained, by way of one or several arrangements, such as the following non-limiting arrangements:

The two mesh components are directly attached to each other at edges of the mesh components;

The two mesh components are directly attached to a part of the envelope surface of the coil-shaped component, i.e. attached to one or several points or locations on the envelope surface of the coil-shaped component.

The fiber of the coil-shaped component is threaded through the mesh structure at one or more locations of the mesh component.

By attaching the mesh components directly to the coil-shaped component, it is possible to leave the edges of the mesh components unattached, i.e. open.

The two mesh components can be directly attached to each other along edges of the mesh components. Different attachment techniques or closing mechanisms can be used to attach the mesh components to each other, such as stitching, suturing, and/or stapling. Each pair of mesh components can be directly attached to each other along all edges but leaving suitable slots where tissue can be filled in after which the slots can be closed by suturing or other suitable closing mechanism.

The two mesh components of a pair of mesh components may have identical or different size and/or shape. In case their size and shape are identical, the projected area of one mesh component should preferably overlap with the projected area of the other mesh component to at least 90%. In case the two mesh components have different sizes, and optionally different shapes, the projected area of the smaller mesh component should be within the projected area of the larger mesh component. In this regard, both projected areas should be directly measured or estimated from a two-dimensional, projected picture, wherein any curvature in the longitudinal plane of each mesh component has been eliminated.

The medical implant may comprise two or more mesh components, wherein the number of mesh components is in a range of including from 1 to 10, such as 1, 2, 3, 4, 5, 6, 7, 8, 9, or 10 mesh components.

In the medical implant, one or more coil-shaped components may be arranged between each pair of two mesh components, wherein the number of coil-shaped components is in a range of including from 1 to 100, such as but not limited to 1, 2, 3, 4, 5, 10, 15, 20, 30, 40, 50, 60, 70, 80, 90, or 100 coil-shaped components. The coil-shaped components arranged between the same two mesh components may be identical or different in size and shape.

In case two or more coil-shaped components are arranged between the same pair of two mesh components, the coil-shaped components can be intertwined or threaded as further explained below. The coil-shaped components can be arranged axially parallel, axially perpendicular, or axially at any angle between 0° and 90° in relation to each other. The coil-shaped components can overlap or intersect each other, or can be separated from each other. In all embodiments of the present disclosure, the helix rotation axis of each coil-shaped component extends in parallel with the projected areas of the two mesh components, as projected in the longitudinal plane of the mesh components.

An example of a suitable arrangement of coil-shaped components being separated from each other is wherein each coil-shaped component enclosed by the same pair of two mesh components is formed as a circle such that its two ends meet, and wherein larger circles thus formed are placed outside smaller circles thus formed (see FIG. 4b). The ends of each coil-shaped component are optionally attached to each other by any suitable attachment technique.

As mentioned above, a pair of mesh components can enclose two or more coil-shaped components, which can be axially intertwined or threaded, either partly or completely overlapping. The two or more coil-shaped components can be of the same or different sizes. A smaller coil-shaped component can be placed inside a larger coil-shaped component. Intertwined coil-shaped components can have the same or different directions of rotation.

A coil-shaped component can for example be produced by winding a fiber around a core element to the desired coiled shape, and then removing the core element. The cross-sectional profile of the coil-shaped component obtains its shape and size directly from the shape and size of the core element. Optionally, the shape of the coil-shaped component can be stabilized by annealing, i.e. heating the fiber while winding it around the core element. The annealing can be achieved by using a heated core element. If annealing is applied in the production process, the temperature should be adapted to the material of the fiber used.

The empty space inside a hollow coil-shaped component (created by the core element used during production of the coil-shaped component, as explained above) and/or between the mesh components can optionally be filled with tissue (e.g. fat tissue and/or muscle tissue) before or at the time of implantation of the medical implant into the body.

The empty space inside a hollow coil-shaped component and/or between the mesh components can optionally be filled with a pharmaceutically active compound or with a pharmaceutical composition comprising a pharmaceutically active compound and any suitable pharmaceutically acceptable adjuvant or carrier. Non-limiting examples of pharmaceutically active compounds are antibiotics and anti-inflammatory agents.

Further, a coil-shaped component can be formed by intertwining two fibers, which have an identical helical form and cross-sectional profile but have opposite rotational directions. Alternatively, the coil-shaped component can be formed by braiding three or more fibers, in which case the fibers are intertwined in such a way that no two fibers are twisted around one another.

The fiber component, which forms both coil-shaped components and mesh components, can be a monofilament, a multifilament or a combination thereof. The fiber can be coaxial, i.e. having two or more layers of material. The fiber may be hollow. The fiber may have a cross-sectional profile which is circular, flat, rectangular, or quadratic or any other shape, such as any irregular shape. The fiber can comprise several different materials, which have different mechanical properties, such as different elasticity, strength, and/or degradation time, to mention a few. The fiber may preferably comprise or consist of degradable material, i.e. material that is resorbable by the body. The fiber may be coated with a pharmaceutically active substance, such as an antibiotic. In the case that the fiber is hollow, the fiber may contain a pharmaceutically active compound and thereby the fiber will act as a carrier for the active compound where the degradable characteristics of the fiber will set the substance delivery time. Non-limiting examples of pharmaceutically active compounds are antibiotics and anti-inflammatory agents.

Suitable materials for the fiber component, which forms both the coil-shaped component and the mesh component, are synthetic materials, preferably degradable materials. Degradable means that the material is resorbable by the body. Examples of suitable materials for the fiber component are, as described in more detail in EP2626454, (a) resorbable polymers with a relatively short degradation time, and non-limiting examples are polymers or copolymers made from the monomer glycolide in pure form, or in combination with paradioxanone, lactide, trimethylene carbonate or caprolactone. Preferably glycolide is present in the highest concentration and can be combined with one or more of the other mentioned monomers in the same material. Yet another monomer can be paradioxanone in its pure form, or in combination with lactide, trimethylene carbonate or caprolactone; (b) resorbable polymers with a relatively long degradation time, and non-limiting examples are polylactide and polyurethanes. Polylactide is preferably made from the monomer L,L-lactide, which can be combined with small amounts of other monomers such as glycolide, trimethylene carbonate or caprolactone to fine tune elastic and degradation properties. Examples of degradable polyurethanes are, but not limited to, polyureaurethanes, polyesterurethanes and polycarbonateurethanes; or (c) any combinations thereof; suitable polymer combinations would, for example, be polyglycolide or blockcopolymers where the main monomer component being glycolide in combination with a small amount of trimethylene carbonate or caprolactone for the first polymer type and blockcopolymers with L,L-lactide as the main monomer component in combination with trimethylene carbonate or caprolactone. Various polyesterurethanes and polycarbonateurethanes would also be of particular use in certain applications, with their long in vivo degradation time and high elasticity.

A suitable mesh component is commercially available under the trade name TIGR® Matrix Surgical Mesh and is sold by the company Novus Scientific. This mesh is described for example in U.S. Pat. Nos. 9,566,370 and 8,083,755. However, although synthetic and degradable materials are believed to be advantageous, a medical support device according to the invention can be made from permanent (non-degradable, non-resorbable) synthetic materials, or even from biological materials.

The medical implant according to the present disclosure is preferably degradable in all its parts, i.e. the coil-shaped component is preferably degradable and the mesh components are preferably degradable. The choice of material degradation time in the body is suitably adapted to the type of medical or cosmetic application the implant is intended for.

A suitable, non-limiting, method of manufacture of a medical implant according to the present disclosure comprises:
 1. Extruding fiber;
 2. Forming a coil-shaped component by winding the fiber around a core having desired shape and form, optionally while applying heat;
 3. Removing the core from each coil-shaped component;
 4. Optionally combining several coil-shaped components into a desired pattern;
 5. Arranging the coil-shaped component or the pattern of coil-shaped components between mesh components.

Presently Preferred Dimensions of the Medical Implant and its Components

The fiber component which is used to produce the coil-shaped component and the mesh components, respectively, has an outer diameter in a range of including from 0.1-3 mm, such as, but not limited to, 0.1, 0.2, 0.5, 1.0, 1.5, 2.0, 2.5, or 3.0.

The length of a mesh component is in a range of including from 20-800 mm, such as, but not limited to, 20, 30, 40, 50, 100, 150, or 200 mm. The width of a mesh component is in a range of including from 10-500 mm, such as, but not limited to, 10, 20, 30, 40, 50, 100, 200, 300, 400, or 500 mm. The thickness or height of a mesh component is in a range of including from 0.1-2 mm, such as, but not limited to, 0.1, 0.2, 0.3, 0.4, 0.5, 1.0, 1.5, or 2.0 mm.

The projected area of each mesh component has a porosity in a range of including from 10% to 80%, preferably in a range of including from 20% to 40%, such as 20%, 30%, or 40%, to adequately promote cellular ingrowth.

As defined above, a distance-building component is a coil-shaped component located between two mesh components. The coil-shaped component creates a distance between the two mesh components. The distance between two mesh components is suitably in the range of including from 2 to 25 mm, preferably in the range including from 2 to 10 This means that the outer diameter or the outer width in the radial direction of the coil-shaped component shall be in the range including from 2 to 25 mm, preferably in the range including from 2 to 10 mm, such as, but not limited to, 2, 3, 4, 5, 6, 7, 8, 9, or 10 mm.

The coil-shaped component has a helical pitch in a range of including from 1-15 mm, such as, but not limited to, 1, 2, 3, 4, 5, 6, 7, 8, 9, 10, 11, 12, 13, 14, or 15 mm.

Clinical Applications

The medical implant according to the present disclosure may be used in various medical applications and/or plastic and reconstructive surgery applications in the body. The basic construction of the medical implant is intended to facilitate and promote regeneration of tissue and/or ingrowth of tissue; primarily soft tissue but not limited thereto. The medical implant may also facilitate regeneration of hard tissue, such as bone tissue. As new tissue is generated, the body will be able to gradually sustain itself. In many applications, it is therefore suitable that the implant gradually degrades over time, which gives the body time to rebuild the tissue and strength needed to become fully self-sustained.

In addition to the above mentioned application, the empty space inside the hollow coil-shaped component and between the mesh components can be filled with tissue, which is to be moved from one position to another position in the body (e.g. fat tissue and/or muscle tissue, depending on the application and location in the body).

Alternatively, or additionally to the previously mentioned application, the construction of the present medical implant makes it possible to use the medical implant as a vehicle for administration of a pharmaceutically active compound or composition to the body, e.g. an antibiotic or an anti-inflammatory agent. For example, the hollow core of the coil-shaped component can be loaded with a pharmaceutical compound, suitably in combination with a pharmaceutically acceptable adjuvant or carrier. The medical implant and/or the pharmaceutically acceptable carrier or adjuvant may be designed such that the pharmaceutically active compound can be released in a controlled manner over a predetermined, suitable amount of time, depending on the intended application. The materials used for a medical implant can be varied such that the degradation time of the implant varies suitably depending on the application and/or the location in the body.

The medical implant according to the present disclosure may for example be used for stabilization of breast prosthesis, tissue augmentation, tissue regeneration, tissue replacement, as a space filler and/or for delivery of a pharmaceutically active compound. The medical implant may be used in the following non-limiting clinical procedures, according to Table 1.

TABLE 1

Examples of clinical procedures

| Procedure | Location in the body |
|---|---|
| Lipo filling | Anywhere |
| Rhinoplasty | Nose |
| Mastopexi | Breast |
| Nipple reconstruction | Breast |
| Facial reconstruction | Face |
| Hernia repair | Anywhere |
| Revision surgery | Breast |
| Breast reconstruction | Breast |
| Abdominal wall reconstruction | Abdominal wall |
| Replace tissue after | Anywhere |
| Replace damaged, burned, diseased tissue e.g. cancer | Anywhere |

The construction of the medical implant according to the present disclosure, i.e. a coil-shaped component lying horizontally between two mesh components, results in a three-dimensional implant which can easily be bent, and which has such a strength in its cross-sectional profile in the z-direction that it can keep its functional three-dimensional form, while being pliable and soft in the x-direction and the y-direction. The construction makes it easy to adapt the implant's cross-sectional profile in all directions (x, y, z) to obtain a suitable fit and geometry for each clinical application. For example, the cross-sectional profile of the coil-shaped component can be wedge-formed and thereby function as an aesthetic transition between a breast implant and the body, to avoid sagging and cavities which would need to be filled out by other methods. A conical shape at both ends of the coil-shaped component, in its axial direction, will allow a soft transition to the mesh components and thereby a soft transition of the medical implant to the body.

In applications of augmentation of tissue, the coil-shaped component(s) can suitably have large helical turns, and thus a center core which is radially wide, and which may act as a carrier for tissue to be inserted at the implantation site.

The fiber component, which is wound to form coil-shaped components and mesh components, can be made for example by extrusion, whereby its properties can be matched against its desired function. There are many suitable materials which can be extruded, and it is possible to combine different materials into several layers. If degradable polymers are used, the implant can have different properties over time.

To further illustrate the scope of the present disclosure, two non-limiting examples of medical implants according to the present disclosure are provided below.

The first example relates to a medical implant which may for example be suitable for breast reconstruction. Such a medical implant may suitably comprise approximately 70 coil-shaped components arranged between two mesh components. The mesh components suitably are each approximately 150×200 mm. The medical implant consisting of one layer of coil-shaped components between two mesh components will suitably have a thickness or height of in a range including from 3-6 mm approximately.

The second example is directed to a medical implant which may for example be suitable as space filler. Such a medical implant may comprise 10 layers of mesh components, each having a largest surface of around 100×100 mm, and approximately 1 to 10 coil-shaped components arranged in a layer between each two mesh components, i.e. up to 100 coils in total. 1 coil-shaped component may be sufficient if it is arranged in an S-form, while up to 10 coil-shaped components may be more suitable if they are arranged in a cross-shaped pattern (see FIG. 4a) or a star-shaped pattern (see FIGS. 5 and 6).

The invention claimed is:
1. A medical implant comprising:
a degradable coil-shaped component and
a first degradable mesh component and a second degradable mesh component;
wherein each mesh component has a largest surface extending in two directions in the x-y plane of the mesh component, and
wherein each mesh component has a projected area, which is said largest surface as projected in the x-y plane of the medical implant;
wherein
the coil-shaped component is arranged between the two mesh components;
the coil-shaped component has a center core which is hollow; and
the coil-shaped component has a helix rotation axis, which extends in parallel with said projected area of the first mesh component and said projected area of the second mesh component,
wherein the coil-shaped component comprises a fiber component, which has been helically wound to form the coil-shaped component,
wherein the coil-shaped component has a helical pitch which is larger than the width of the fiber component which forms the coil-shaped component, wherein said width is measured in the direction of the helix rotation axis,
wherein said helical pitch of the coil-shaped component is in a range of from 1 to 15 mm.
2. The medical implant according to claim 1, wherein a cross-sectional profile of the coil-shaped component has a hollow center core area, which is larger than a cross-sectional area of the fiber component which forms the coil-shaped component.

3. The medical implant according to claim 1, wherein a cross-sectional profile of the coil-shaped component is axially constant or variable in size, and/or is axially constant or variable in shape.

4. The medical implant according to claim 1, wherein the coil-shaped component is formed as a circle, an oval, a rectangle, an S-form, a straight line, a U-turn, or any other irregular form, between said two mesh components, in a plane parallel to said projected areas of the mesh components.

5. The medical implant according to claim 1, wherein the coil-shaped component is contained between said two mesh components.

6. The medical implant according to claim 1, wherein said two mesh components are attached to each other at edges of the mesh components.

7. The medical implant according to claim 1, wherein said two mesh components are attached to a part of an envelope surface of the coil-shaped component.

8. The medical implant according to claim 1, wherein said two mesh components are attached to the coil-shaped component by threading a loop of the coil-shaped component through each mesh component.

9. The medical implant according to claim 1, wherein the number of mesh components is in a range of from 2 to 10, and wherein at least one coil-shaped component is arranged between each two mesh components.

10. The medical implant according to claim 1, wherein a number of coil-shaped components arranged between each two mesh components is in a range of from 1 to 100.

11. The medical implant according to claim 10, wherein coil-shaped components arranged between the same two mesh components are intertwined, overlapping, braided, axially aligned, axially perpendicular, axially at an angle of between 0° and 90°, and/or are separated from each other.

12. The medical implant according to claim 6, wherein said two mesh components are attached to each other at edges of the mesh components by suturing, stapling, or gluing.

13. The medical implant according to claim 7, wherein said two mesh components are attached to a part of the envelope surface of the coil-shaped component by stitching or suturing.

14. A medical implant comprising:
a degradable coil-shaped component and
a first degradable mesh component and a second degradable mesh component;
wherein each mesh component has a largest surface extending in two directions in the x-y plane of the mesh component, and
wherein each mesh component has a projected area, which is said largest surface as projected in the x-y plane of the medical implant;
wherein
the coil-shaped component is arranged between the two mesh components;
the coil-shaped component has a center core which is hollow; and
the coil-shaped component has a helix rotation axis, which extends in parallel with said projected area of the first mesh component and said projected area of the second mesh component,
wherein said two mesh components are attached to a part of an envelope surface of the coil-shaped component by stitching or suturing.

15. A medical implant comprising:
a degradable coil-shaped component and
a first degradable mesh component and a second degradable mesh component;
wherein each mesh component has a largest surface extending in two directions in the x-y plane of the mesh component, and
wherein each mesh component has a projected area, which is said largest surface as projected in the x-y plane of the medical implant;
wherein
the coil-shaped component is arranged between the two mesh components;
the coil-shaped component has a center core which is hollow; and
the coil-shaped component has a helix rotation axis, which extends in parallel with said projected area of the first mesh component and said projected area of the second mesh component,
wherein said two mesh components are attached to the coil-shaped component by threading a loop of the coil-shaped component through each mesh component.

16. The medical implant according to claim 1, wherein a cross-sectional profile of the coil-shaped component is conical, and/or is from oval to rectangular shape.

* * * * *